United States Patent [19]

Budde

[11] 4,256,096

[45] Mar. 17, 1981

[54] MATTRESS ASSEMBLY FOR TREATMENT OF PATIENTS

[76] Inventor: Richard B. Budde, 506 Oak St., Cincinnati, Ohio 45219

[21] Appl. No.: 60,647

[22] Filed: Jul. 25, 1979

[51] Int. Cl.³ .............................................. A61F 5/00
[52] U.S. Cl. ........................................... 128/70; 5/433
[58] Field of Search .............. 128/70; 5/68, 433, 434, 5/446, 464, 465, 481

[56] References Cited

U.S. PATENT DOCUMENTS

| 263,625 | 8/1882 | Taylor. | |
|---|---|---|---|
| 1,885,974 | 11/1932 | Winn. | |
| 2,046,645 | 7/1936 | Mason | 5/91 |
| 2,207,095 | 9/1939 | Hutchinson | 5/345 |
| 3,343,531 | 9/1967 | Thompson | 128/69 |
| 3,419,920 | 1/1969 | Maddux et al. | 5/465 |
| 3,747,916 | 7/1973 | Benson | 128/70 |
| 3,998,218 | 12/1976 | Lane et al. | |
| 3,775,785 | 12/1973 | Mittendorf | 5/341 |
| 3,952,346 | 4/1976 | Carlson | 5/433 |
| 4,086,673 | 5/1978 | Hanson | 5/446 |

FOREIGN PATENT DOCUMENTS 7309246 10/1974 Netherlands ............................. 128/70

*Primary Examiner*—Robert W. Michell
*Assistant Examiner*—T. J. Wallen
*Attorney, Agent, or Firm*—Wood, Herron & Evans

[57] ABSTRACT

A surgical mattress assembly including a base mattress, a body support pad mounted on the base mattress, a narrow head support pad, a wide head support pad, means for selectively attaching the head support pads to the end of the body support pad and positioned on the base mattress, and a wedge-shaped shoulder support pad insertable between the base mattress and the body support pad.

8 Claims, 5 Drawing Figures

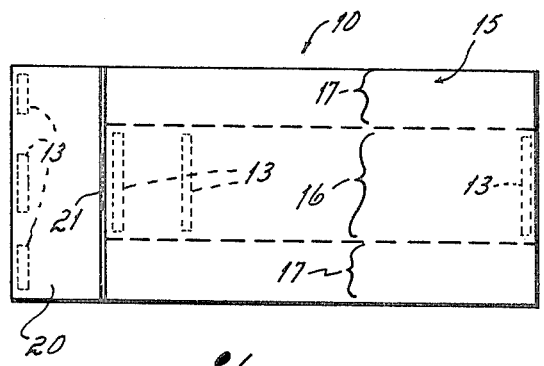
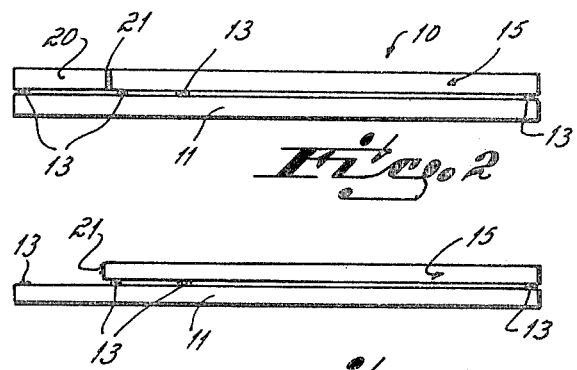
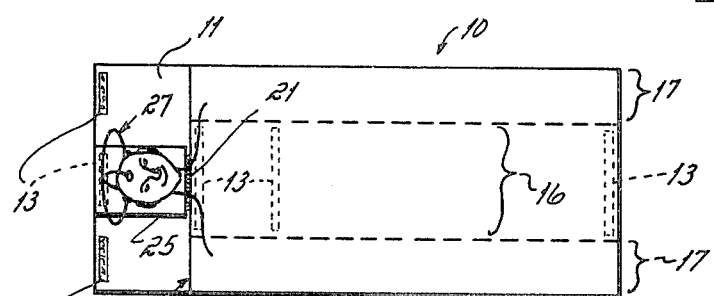

MATTRESS ASSEMBLY FOR TREATMENT OF PATIENTS

This invention relates to mattresses, and more particularly, the invention is directed to an assembly of mattress or body support sections employed in the treatment of patients, particularly those having neck and spine injuries.

Patients having neck and spine injuries must be specially positioned during the period of recovery from injury so as to orient the patient's body properly with particular attention to the relationship of the patient's head to his cervical spine.

There exist in the prior art orthopedic beds for positioning the patient's body in differing attitudes. These beds have plural sections which can be shifted with respect to each other. They are, in general, rather complex and cumbersome mechanical devices which are used primarily during a relatively brief period for treating a patient as contrasted to the supporting of the body of the patient over the much longer period during his convalescence.

An objective of the present invention has been to provide a simple and inexpensive support for a patient which admits of optional modes for support of the patient depending upon the particular needs of the patient.

This objective of the invention is attained by providing a mattress assembly including a base mattress, a body support pad mountable on the base mattress for supporting the patient from his shoulders to his feet, a narrow head support pad, a wide head support pad and a shoulder wedge. The body support pad is at least partly formed of a foam which is softenable by body heat to conform to the contours of the patient's body.

In this assemblage of mattress and pad elements, the base mattress and body support pad are always used. The configuration of the support provided by these is modified through the use of the other three pads, thereby providing the differing support for the patient as follows:

(a) Support for the patient in normal position.

The body support pad and wide head support pad are butted together to provide a full length support pad overlying the base mattress.

(b) Shoulders elevated with respect to head for extension of cervical spine.

The wide head support pad is removed and the patient is supported from the shoulders to his feet on the body support pad with the head inclined downwardly and resting on the base mattress. In this position the patient's cervical spine has a desired extension for recuperation.

(c) Shoulders elevated with respect to the head— heavy patient.

In this configuration, the wedge-shaped shoulder support is positioned between the shoulder end of the body support pad and the base mattress so as to elevate the shoulder area of the body support pad. This configuration is used for a heavy patient who needs to maintain his shoulders elevated substantially with respect to his head but whose body weight tends to compress the support pad to the extent that the proper extension of the cervical spine is not attained. The wedge adds the needed shoulder elevation.

(d) Normal position—head tongs applied to the patient.

The narrow head support pad is placed in abutment with the body support pad so that the patient's head is supported for normal resting position. The narrow pad, nevertheless, permits the patient the freedom to roll his head from side to side without having that movement being interfered with by the head tongs impinging on the head support pad.

The several features of the invention will become more readily apparent from the following detailed description taken in conjunction with the accompanying drawings in which:

FIG. 1 is a top plan view of the invention with the wide head pad in position;

FIG. 2 is a side elevational view of the structure of FIG. 1;

FIG. 3 is a side elevational view of the structure of FIG. 1 with the head support pad removed;

FIG. 4 is a top plan view of the assembly with the narrow head pad in place; and FIG. 5 is a side elevational view of the assembly with the shoulder wedge inserted and the head pad removed.

The mattress assembly indicated at 10 includes a full body length and width base mattress 11 which is formed of conventional foam rubber and preferably is approximately 3"×36"×84". The base mattress has Velcro strips applied at 13 which cooperate with similar strips on the support pads to prevent sidewise slipping of the support pads which are mounted on the base mattress.

The assembly further includes a body support pad 15 approximately 3"×36"×70" having Velcro strips on its undersurface which are alignable with and are engageable with the Velcro strips 13 on the base mattress. The body support pad preferably is formed by a central longitudinally-extending section of body heat-softenable foam 16 and two outboard sections 17 of conventional foam rubber.

The heat-softenable foam as, for example TEMPER FOAM ®, manufactured by Edmont Wilson, is an expensive material which softens upon body contact and tends to flow around the body contour to provide uniform, comfortable support without hard spots which give rise to soreness and pain over long periods. The conventional foam rubber used for the outboard sections (approximately 9 inches in width) is less expensive.

The base mattress 11 and body support pad 15 are the primary elements of the assembly and are employed in all of the configurations contemplated by the invention.

A wide head support pad 20 (approximately 3"×14"×36") is mountable on the base mattress in abutting relation to the body support pad to create a normal size support for the patient. It is preferably formed of foam rubber and has, on its undersurface, Velcro strips which mate with the Velcro strips 13 of the base mattress. Preferably, the body support pad 15 and the side head support pad 20 have on their abutting edges mating Velcro strips as at 21 to keep the pads properly aligned.

The assembly also includes a narrow head support pad 25 (approximately 3"×14"×10") also formed of conventional foam rubber. The narrow pad has a Velcro strip on its undersurface to mate with the central Velcro strip 13 on the base mattress and it has a Velcro strip to mate with the body support pad Velcro strip 21 at the abutting edges of the two pads as shown in FIG. 4.

The assembly further includes a shoulder support wedge 26 which is of foam rubber. That wedge or pad is preferably of the same width as the body support pad and has a longitudinal dimension of about 18 inches. It is triangular in cross section having a base of approximately 3 inches.

In use, the body support pad 15 and wide head support pad 20 are mounted in abutting relation and positioned on the base mattress 11 to provide full normal support for the patient. If a patient is required to wear head tongs 27, the narrow head pad 25 is substituted for the wide head pad and placed in abutting relation to the body support pad to provide the configuration of FIG. 4. There it can be seen that the head of the patient can be turned slightly without interference by the tongs impinging upon the mattress or pads. If the injury to the patient requires the shoulders to be elevated with respect to the head, the configuration of FIG. 3 is employed wherein only the body support pad is positioned on top of the base mattress 11. In this attitude, the patient's body up to his shoulders is supported on the body support pad and his head is permitted to hang downwardly, resting on the base mattress.

Finally, when a quite heavy patient needs the same type of support as provided by the organization of FIG. 3, the shoulder support wedge is inserted under the end of the body support pad as shown in FIG. 5 and is maintained there by the mating Velcro strips at 13. The heavier patient compresses the foam padding to a greater extent than the lighter patient, but his head will hang below the shoulders resting on the base mattress for the desired extension of the cervical spine during his recuperation.

Having described my invention, I claim:

1. A patient support for use in the treatment of spine injuries, comprising
    a base mattress,
    a body pad for positioning on the mattress, the body pad having a length shorter than the mattress and providing support of the body but not the head of a patient lying thereon, and
    a series of head and shoulder support pads, each removably attachable to at least one of said mattress and body pad,
    said series of pads comprising,
    a first head support pad which, when positioned on said mattress abutting a head end of said body pad, provides support for the head of said patient,
    the body pad when said first head support pad is removed therefrom supporting the body of said patient while his head rests at a lower level so that the patient's head and neck are in extension,
    said series of pads also including a second head support pad having a width substantially less than that of said mattress, the second head support pad attachable to at least one of said mattress and body pad for supporting a patient's head to which a skull tong has been applied,
    a shoulder support pad of tapering thickness and positionable between the body pad and the mattress to provide additional support for the shoulders of a heavy patient during such extension, said shoulder support pad having its greatest thickness adjacent the head end of said body pad and tapering to a minimum thickness in the direction toward the patient's pelvis.

2. The support of claim 1 wherein said body pad is made at least in part of a foam which softens under the patient's body heat to conform to the shape of the patient's body, thereby to relieve pressure points on the skin.

3. The support of claim 1 wherein said first and second head supports are each removably attachable to both said mattress and said head end of said body pad.

4. The support of claim 1 wherein said shoulder support pad tapers from a thickness at one end which is substantially equal to that of said first head support, to a minimum thickness at its opposite end.

5. The support of claim 4 wherein said shoulder support pad is removably securable between said mattress and said body pad.

6. The support of claim 1 wherein said second head support pad has a width which is less than half that of said mattress, and
    said second head support pad is attachable to the head end of said body pad, at a central position with respect thereto.

7. The support of claim 1 wherein the body pad is removably securable to the base mattress.

8. A patient support for use in the treatment of spine injuries, comprising
    a base mattress,
    a body pad for positioning on the mattress, the body pad having a length shorter than the mattress and providing support of the body but not the head of a patient lying thereon, and
    a series of head and shoulder support pads, each removably attachable to at least one of said mattress and body pad,
    said series of pads comprising,
    a first head support pad which, when positioned on said mattress abutting a head end of said body pad, provides support for the head of said patient,
    the body pad when said first head support pad is removed therefrom supporting the body of said patient while his head rests at a lower level so that the patient's head and neck are in extension,
    said series of pads also including a second head support pad having a width substantially less than that of said mattress, the second head support pad attachable to at least one of said mattress and body pad for supporting a patient's head to which a skull tong has been applied,
    a shoulder support pad of tapering thickness and positionable between the body pad and the mattress to provide additional support for the shoulders of a heavy patient during such extension, said shoulder support pad having its greatest thickness adjacent the head end of said body pad and tapering to a minimum thickness in the direction toward the patient's pelvis,
    said body pad comprising,
    a central portion of a foam which softens under the patient's body heat to conform to the shape of the patient's body, thereby to relieve pressure points on the skin, and
    side portions of non-body heat softenable foam, said side portions being secured to each side of said central portion.

* * * * *